(12) United States Patent
Narayanan et al.

(10) Patent No.: US 11,850,068 B2
(45) Date of Patent: Dec. 26, 2023

(54) MODULAR SENSING UNIT

(71) Applicant: INTERNATIONAL BUSINESS MACHINES CORPORATION, Armonk, NY (US)

(72) Inventors: Rajeev Narayanan, Briarcliff Manor, NY (US); Bing Dang, Chappaqua, NY (US); Katsuyuki Sakuma, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 550 days.

(21) Appl. No.: 16/697,284

(22) Filed: Nov. 27, 2019

(65) Prior Publication Data

US 2021/0153811 A1 May 27, 2021

(51) Int. Cl.
*A61B 5/00* (2006.01)
*H01B 9/00* (2006.01)

(52) U.S. Cl.
CPC .......... *A61B 5/6826* (2013.01); *A61B 5/0002* (2013.01); *A61B 5/0017* (2013.01); *A61B 2562/222* (2013.01); *H01B 9/003* (2013.01)

(58) Field of Classification Search
None
See application file for complete search history.

(56) References Cited

U.S. PATENT DOCUMENTS

| | | | | |
|---|---|---|---|---|
| 4,830,014 A * | 5/1989 | Goodman | ............ | A61B 5/6838 600/479 |
| 5,168,759 A | 12/1992 | Bowman | | |
| 5,776,059 A * | 7/1998 | Kaestle | ................... | A61B 5/411 600/340 |
| 6,018,673 A * | 1/2000 | Chin | .................. | A61B 5/14552 600/323 |
| 6,144,868 A * | 11/2000 | Parker | .................. | A61B 5/6826 600/344 |
| 6,360,615 B1 | 3/2002 | Smela | | |
| 6,515,669 B1 * | 2/2003 | Mohri | ..................... | G06F 3/017 345/474 |
| 8,626,472 B2 | 1/2014 | Solinsky | | |
| 9,822,002 B1 | 12/2017 | Andry | | |
| 9,931,063 B2 * | 4/2018 | Aita | ....................... | A61B 5/411 |
| 10,085,689 B1 * | 10/2018 | Giuffrida | ............. | A61B 5/6826 |
| 2004/0147818 A1 * | 7/2004 | Levy | ...................... | A61B 5/002 600/300 |
| 2005/0059869 A1 * | 3/2005 | Scharf | ................ | A61B 5/14552 600/340 |

(Continued)

OTHER PUBLICATIONS

Amjadi et al., "Stretchable, Skin-Mountable, and Wearable Strain Sensors and Their Potential Applications: A Review." Advanced Functional Materials, vol. 26, No. 11, Mar. 15, 2016, pp. 1678-1698.

(Continued)

*Primary Examiner* — Carl H Layno
*Assistant Examiner* — Manolis Pahakis
(74) *Attorney, Agent, or Firm* — Brandon L. Stephens; Kristofer L. Haggerty

(57) ABSTRACT

A method, a structure, and a computer system for a modular sensing unit. The structure comprises a sensor module, a power cable ribbon, and a component module, wherein the component module is in communication with and detachable from the sensor module via the power cable ribbon.

10 Claims, 7 Drawing Sheets

(56) References Cited

U.S. PATENT DOCUMENTS

| | | | |
|---|---|---|---|
| 2005/0096554 A1* | 5/2005 | Dudik | A61B 5/6826 600/500 |
| 2007/0073128 A1* | 3/2007 | Hoarau | A61B 5/6844 600/340 |
| 2007/0078315 A1* | 4/2007 | Kling | A61B 5/6829 600/323 |
| 2007/0123763 A1* | 5/2007 | Al-Ali | A61B 5/6832 600/344 |
| 2007/0161877 A1* | 7/2007 | Arai | A61B 18/203 600/316 |
| 2007/0260129 A1* | 11/2007 | Chin | A61B 5/6816 600/323 |
| 2007/0294890 A1* | 12/2007 | Gisin | H01L 23/49827 333/260 |
| 2008/0058622 A1* | 3/2008 | Baker | A61B 5/6826 600/323 |
| 2008/0076995 A1* | 3/2008 | Hoarau | A61B 5/6826 600/344 |
| 2008/0221422 A1* | 9/2008 | Rantala | A61B 5/291 600/383 |
| 2009/0278798 A1* | 11/2009 | Kim | G06F 3/017 345/158 |
| 2010/0063779 A1* | 3/2010 | Schrock | A61B 5/742 73/862.627 |
| 2010/0317936 A1* | 12/2010 | Al-Ali | A61B 46/10 600/323 |
| 2011/0152725 A1* | 6/2011 | Demir | A61B 5/103 600/587 |
| 2011/0160553 A1* | 6/2011 | Talbot | A61B 5/14514 600/365 |
| 2011/0267042 A1* | 11/2011 | Sano | A61B 5/1125 324/207.11 |
| 2011/0273839 A1* | 11/2011 | Villegas | A61B 5/742 361/679.41 |
| 2012/0065514 A1* | 3/2012 | Naghavi | G01K 13/20 600/481 |
| 2013/0144141 A1* | 6/2013 | Chin | A61B 5/14552 600/344 |
| 2013/0158365 A1* | 6/2013 | Chey | A61B 5/14503 600/595 |
| 2013/0237782 A1* | 9/2013 | Lisogurski | G16H 40/63 600/323 |
| 2013/0274587 A1* | 10/2013 | Coza | A61B 5/0002 600/595 |
| 2014/0200486 A1* | 7/2014 | Bechtel | A61B 5/1036 600/592 |
| 2014/0221799 A1* | 8/2014 | Rajagopal | A61B 5/6867 600/407 |
| 2014/0347491 A1* | 11/2014 | Connor | A61B 5/1114 348/158 |
| 2014/0349256 A1* | 11/2014 | Connor | A47G 21/02 434/127 |
| 2015/0297079 A1* | 10/2015 | Tateda | A61B 5/0015 600/340 |
| 2015/0330855 A1* | 11/2015 | Daniecki | A61B 5/6807 73/725 |
| 2015/0342521 A1* | 12/2015 | Narita | A61B 5/4893 600/546 |
| 2016/0098080 A1* | 4/2016 | Chen | G06F 3/0346 345/173 |
| 2016/0166157 A1* | 6/2016 | Naghavi | A61B 5/02007 600/479 |
| 2016/0198996 A1* | 7/2016 | Dullen | A61B 5/4824 600/595 |
| 2016/0235341 A1* | 8/2016 | Choi | A61B 5/6898 |
| 2016/0278665 A1* | 9/2016 | Ferreira | A61B 5/6826 |
| 2016/0313798 A1* | 10/2016 | Connor | A61B 5/1125 |
| 2016/0324442 A1* | 11/2016 | Zdeblick | A61B 5/0537 |
| 2017/0273599 A1* | 9/2017 | Reese | A61B 5/6807 |
| 2017/0348156 A1* | 12/2017 | Duesterhoft | A61F 13/064 |
| 2018/0008146 A1* | 1/2018 | Al-Ali | A61B 5/6829 |
| 2018/0020931 A1* | 1/2018 | Shusterman | A61N 1/3627 600/483 |
| 2018/0085061 A1* | 3/2018 | Heisig | G01B 7/20 |
| 2018/0093121 A1* | 4/2018 | Matsuura | G09B 19/0038 |
| 2018/0296132 A1* | 10/2018 | Yamaji | A61B 5/4806 |
| 2018/0300514 A1* | 10/2018 | Afzali-Ardakani | G01D 18/00 |
| 2018/0368710 A1* | 12/2018 | Yang | A61B 5/0205 |
| 2019/0094088 A1* | 3/2019 | Reif | A61B 5/6807 |
| 2019/0117157 A1* | 4/2019 | Hu | G01K 3/10 |
| 2019/0120708 A1* | 4/2019 | Kothandaraman | H01L 22/34 |
| 2019/0187010 A1* | 6/2019 | Knickerbocker | G01L 1/225 |
| 2019/0246926 A1* | 8/2019 | Virag | A61B 5/361 |
| 2019/0254541 A1* | 8/2019 | Di Achille | A61B 5/02125 |
| 2019/0332140 A1* | 10/2019 | Wang | G06F 3/011 |
| 2019/0336020 A1* | 11/2019 | Kranz | A61B 5/318 |
| 2019/0347479 A1* | 11/2019 | Sakuma | G06V 30/333 |
| 2019/0378615 A1* | 12/2019 | Martin | A61B 5/282 |
| 2020/0008299 A1* | 1/2020 | Tran | H05K 1/0386 |
| 2020/0026352 A1* | 1/2020 | Wang | G06F 3/044 |
| 2020/0121204 A1* | 4/2020 | Sakuma | A61B 5/1072 |
| 2020/0205735 A1* | 7/2020 | Narayanan | G06F 3/017 |
| 2020/0253516 A1* | 8/2020 | Cronin | A61B 5/6826 |
| 2021/0100460 A1* | 4/2021 | Dagdeviren | G01C 19/00 |
| 2021/0121080 A1* | 4/2021 | Narayanan | A61B 5/0205 |
| 2021/0121128 A1* | 4/2021 | Pancoast | A61B 5/682 |
| 2021/0330516 A1* | 10/2021 | Letourneau | A61B 5/6826 |
| 2022/0100272 A1* | 3/2022 | Patnaikuni | A61B 5/1101 |

OTHER PUBLICATIONS

Cohen et al., "IBM Research shows how health insights may come from fingernail wearable," Tech Xplore, Dec. 24, 2018 [Accessed Mar. 25, 2019] https://techxplore.com/news/2018-12-ibm-health-insights-fingernail-wearable.html, pp. 1-3.

Hsiu et al., Nail+: sensing fingernail deformation to detect finger force touch interactions on rigid surfaces. In Proceedings of the 18th International Conference on Human-Computer Interaction with Mobile Devices and Services (MobileHCI '16). ACM, 2016, pp. 1-6.

Mell et al., "The NIST Definition of Cloud Computing", National Institute of Standards and Technology, Special Publication 800-145, Sep. 2011, pp. 1-7.

Sakuma et al., "Wearable Nail Deformation Sensing for Behavioral and Biomechanical Monitoring and Human-Computer Interaction." Scientific Reports, vol. 8, article No. 18031, Dec. 2018. https://www.nature.com/articles/s41598-018-36834-x, pp. 1-11.

\* cited by examiner

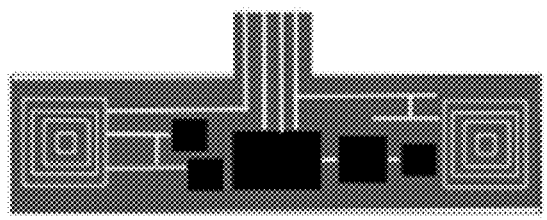 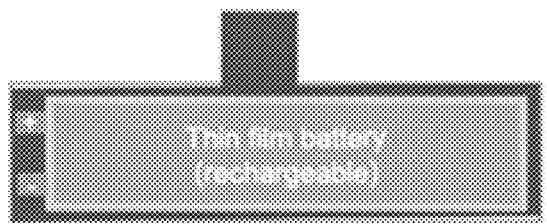
Top side: microcontroller, memory, Cu traces, accelerometer, gyroscope, antenna, etc.
Bottom side: flexible thin film batteries( single or multiple cells)
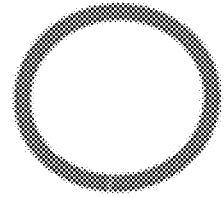 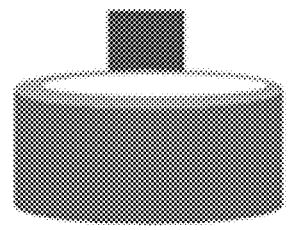
After wrapping, the flex circuit forms a ring or "bandage" shape
FIG. 7

MODULAR SENSING UNIT

BACKGROUND

The exemplary embodiments relate generally to sensors, and more particularly to a modular sensor unit.

Sensors are devices which detect or measure a physical property. Sensors have become ubiquitous in everyday items such as smart devices and vehicles due to their ability to gather useful information at relatively low costs, however some challenges still remain. For example, while many sensors can be produced in very small sizes, housing additional components needed to measure, amplify, convert, process, and transmit the signal pose challenges to achieving small form factors or placing sensors in ideal locations. Moreover, components of such sensors may have limited life and need frequent replacing.

SUMMARY

The exemplary embodiments disclose a method, a structure, and a computer system for a modular sensing unit. The structure comprises a sensor module, a power cable ribbon, and a component module, wherein the component module is in communication with and detachable from the sensor module via the power cable ribbon.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which:

FIG. 7 depicts an exemplary use case of the modular sensor 110, in accordance with the exemplary embodiments.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
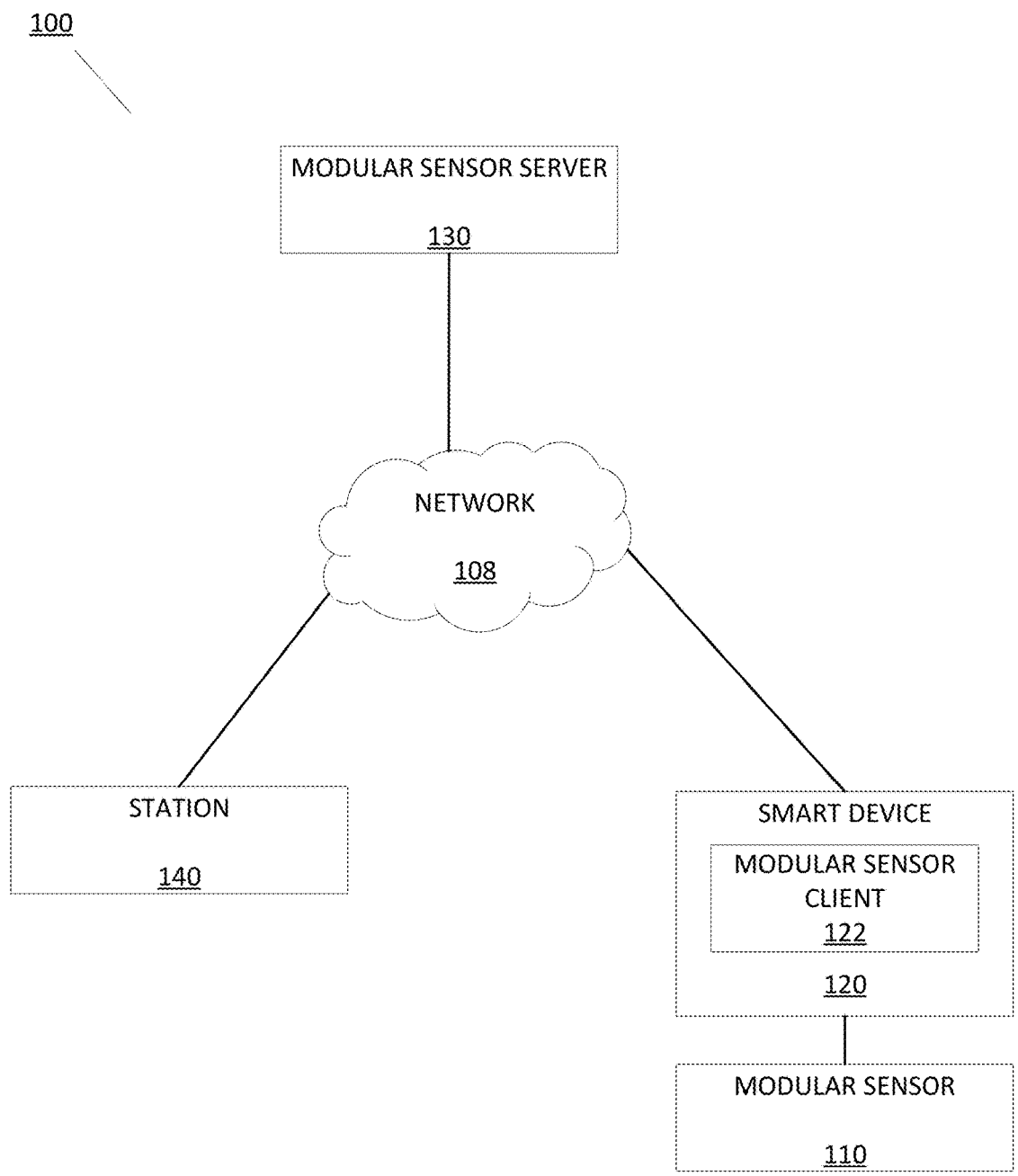
FIG. 1 depicts an exemplary schematic diagram of a modular sensor system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Sensors are devices which detect or measure a physical property. Sensors have become ubiquitous in everyday items like smart devices and vehicles due to their ability to gather useful information at relatively low costs, however some challenges still remain. For example, while many sensors can be produced in very small sizes, housing additional components needed to measure, amplify, convert, process, and transmit the signal pose challenges to achieving small form factors or placing sensors in ideal locations. Moreover, some sensors may have limited life and need frequent replacing.

For example, strain gauges are sensors used to convert a change in electrical resistance into a mechanical strain. The change in resistance is caused by deformation of the strain gauge, and the resistance change is often measured using devices such as a Wheatstone bridge. The change in resistance may then be amplified, converted from an analog to digital signal, and processed into a strain before being transmitted as needed. Though strain gauges sensors may be produced in very small sizes, housing the additional components needed to measure, amplify, convert, process, and transmit the signal pose challenges to achieving small form factors. Moreover, such strain gauge sensors themselves may wear out or otherwise lose functionality prior to that of other components.

Therefore, a solution is needed for a sensor device that is versatile for applications having specific size, shape, fit, comfort, or other demands, such as applications requiring a small form factor, minimal invasiveness, or lack of obstruction. Moreover, a solution is needed that provides for replaceable and modular sensor components, such as strain gauges, as such components degrade or lose functionality over time.

Accordingly, exemplary embodiments disclose a modular sensor system. Highlights and improvements of the exemplary embodiments include reduced sensor form factor, increased flexibility in sensor placement, reduced sensor obstruction, decreased sensor invasiveness, increased contact of the sensor with a surface, improved placement of the sensor, increased sensor ergonomics, increased sensor flexibility, increased sensor applicability, increased sensor unit life, increased sensor accuracy, increased sensor flexibility, increased sensor data collection, etc. It will be appreciated that although the exemplary embodiments may reference a strain gauge sensor in order to illustrate the invention, other embodiments may be equally applicable to other sensory equipment, such as a temperature sensor, gyroscope, accelerometer, etc.

FIG. 1 depicts the modular sensor system 100, in accordance with exemplary embodiments. According to the exemplary embodiments, the modular sensor system 100 may include a modular sensor 110, a smart device 120, and a modular sensor server 130, which may be interconnected via a network 108. While the example embodiment illustrates the modular sensor 110 in communication with the smart device 120 and the modular sensor server 130 via the modular sensor client 122 and the network 108, in other embodiments the modular sensor 110 may be a standalone device. Similarly, while programming and data of the exemplary embodiments may be stored and accessed remotely across several servers via the network 108, programming and data of the exemplary embodiments may alternatively or additionally be stored locally on as few as one physical computing device or amongst other computing devices than those depicted. The operations of the modular sensor system 100 are described in greater detail herein.

In the exemplary embodiments, the network 108 may be a communication channel capable of transferring data between connected devices. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. The network 108 may operate in frequencies including 2.4 gHz and 5 gHz internet, near-field communication, Z-Wave, Zigbee, etc. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In exemplary embodiments, the sensor 110 may be a device capable of measuring a physical property and biological information such as heart rate and SPO2. The sensor 110 may be, for example, a strain gauge, a temperature sensor, an optical sensor, an accelerometer, a gyroscope, a vibration sensor, etc. In embodiments, the modular sensor 110 may be in communication with other devices via the network 108, for example through Wi-Fi or NFC (Near-field communication) or Bluetooth connections. Moreover, the modular sensor 110 may include components such as a bridge, an amplifier, analog to digital converter (ADC), processor, a battery, a wireless transmitter, an antenna, etc. The modular sensor 110 is described in greater detail with respect to FIG. 2-10.

In exemplary embodiments, the smart device 120 includes a modular sensor client 122, and may be a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 8, as part of a cloud implementation with reference to FIG. 9, and/or as utilizing functional abstraction layers for processing with reference to FIG. 10.

The modular sensor client 122 may act as a client in a client-server relationship, and may be a software and/or hardware application capable of communicating with and providing a user interface for a user to interact with a server and other computing devices via the network 108. Moreover, in the example embodiment, the modular sensor client 122 may be capable of transferring data from the modular sensor 110 and/or the smart device 120 to and from other devices via the network 108. In embodiments, the modular sensor client 122 may utilize various wired and wireless connection protocols for data transmission and exchange, including Bluetooth, 2.4 gHz and 5 gHz internet, near-field communication, Z-Wave, Zigbee, etc. The modular sensor client 122 is described in greater detail with respect to FIG. 2-10.

In the exemplary embodiments, the modular sensor server 130 may act as a server in a client-server relationship with the modular sensor client 124. In embodiments, the modular sensor server 130 may receive data from the modular sensor 110 and/or the smart device 120 via the network 108 and/or the modular sensor client 122. The modular sensor server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the modular sensor server 130 is shown as a single device, in other embodiments, the modular sensor server 130 may be comprised of a cluster or plurality of computing devices, working together or working independently. The modular sensor server 130 is described in greater detail as a hardware implementation with reference to FIG. 8, as part of a cloud implementation with reference to FIG. 9, and/or as utilizing functional abstraction layers for processing with reference to FIG. 10.

In the exemplary embodiments, the station 140 may be a device capable of housing, charging, transferring data to and from, etc. the modular sensor 110 or components thereof. In the example embodiment, the station 140 may be capable of receiving components of the modular sensor 110 and charging the components in a wired or wireless fashion for remote use. In addition, the station 140 may be further capable of transferring data between the modular sensor 110 and the modular sensor server 130 via a wired or wireless connection and the network 108. The station 140 is described in greater detail with respect to FIG. 2-10.

Figure 2:
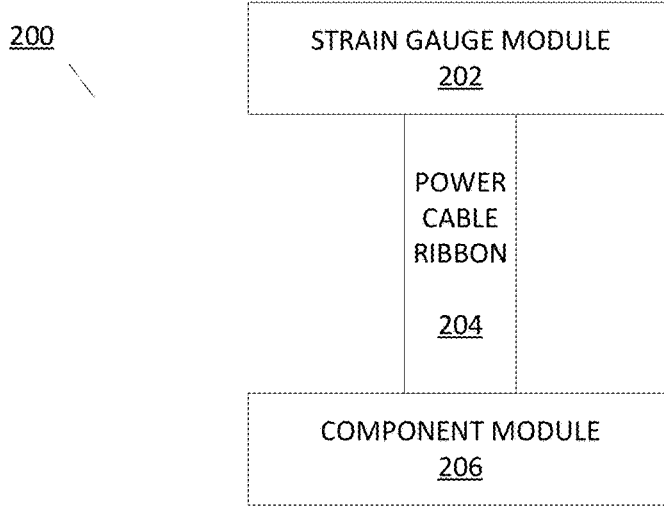
FIG. 2 depicts an exemplary schematic diagram 200 of a modular sensor 110 of the module strain gauge system 100, in accordance with the exemplary embodiments.

FIG. 2 depicts an exemplary schematic of the modular sensor 110 of the modular sensor system 100, in accordance with the exemplary embodiments. In the example embodiment, the modular sensor 110 is portrayed as implementing a modular strain gauge device for sensing strain on a surface. However, in other embodiments, the modular sensor 110 may implement any modular sensing unit, such as an accelerometer or temperature sensor. In the exemplary embodiments, the modular sensor 110 may comprise a strain gauge module 202, a power cable ribbon 204, and a component module 206.

In embodiments, the modular sensor 110 may be modular, and therefore components of the modular sensor 110 may be removed, modified, replaced, recharged, etc., after a set period of time or use. Moreover, the modular sensor 110 or aspects thereof may be housed in the station 140 (depicted by FIG. 1) for data transfer, charging, etc. For example, the strain gauge module 202 may be replaced after the strain gauge module 202 is no longer able to provide measurements beyond a threshold accuracy. In another example, the power cable ribbon 204 and the component module 206 may be separated from the strain gauge module 202 and the component module 206 may be placed in the station 140 in order to recharge an integrated battery. Alternatively, the power cable ribbon 204 and a component module 206 may be removed when data collection from the strain gauge module 202 is no longer needed.

Moreover, positioning of the components within the modular sensor 110 may vary based on application. For example, batteries, microcontrollers, wireless adapters, and other components may be relocated based on application, fit, wearer, type of device, etc. It will be appreciated by one skilled in the art that separating the component module 206 from the strain gauge module 202 may reduce a total package thickness for the modular sensor 110, leaving more flexibility and real estate for other components, such as extended space for a battery, antenna, etc., in the component module 206. In addition, integrated signal processing and edge computing units can reduce the burden of data streaming and wireless communication on the modular sensor 110. Moreover, a shape of sensors can be customized to collect signals relevant to various metrics, conditions, diseases, etc.

In embodiments, electrical components of the modular sensor 110 may be formed on a flexible electronics substrate. The substrate may comprise films, flexible integrated wiring layers that include sensors, a micro controller, a Bluetooth adapter, and a battery (described in greater detail herein). The flexible electronic package wiring can use thinned metal layers/alloys of noble metals or conductive adhesive materials, such as thin Pt, Au, or composite layers of TiNiPt or TiNiAu. The module sensor 110 may implement carbon and silver conductive adhesives, or Ti—Ni—Cu films with flex compatible designs with or without proper moisture barrier or packaging seals. Moreover, the module sensor 110 may utilized thinned layers of polymer and SiOx-SiN repeating layers or thin polymer layers with Ti and/or SiN layers. Moreover, alternating ultra-thin layers of Ti and/or SiN and polymers with each layer being <20 nm to 50 nm may be repeated to create a flexible hermetic package of thickness typically <0.5 um to 50 um. The modular sensor 110 may implement bio-compatible polymers such as topaz, liquid crystal dielectric, polyimide, BCB, PET or other polymers, as well as apply surface coatings to seal packages with a Ti—Ni—Cu—Au layers or alternate compositions. In general, the components of modular sensor 110 may be integrated into any suitable substrate. Detailed descriptions of the component module 206 follows.

In embodiments, the strain gauge module 202, as well as other components of the module sensor 110, may be or implement an adhesive, peelable structure similar to an adhesive bandage. The peelable structure may be adhered to the surface of objects/humans/animals for detecting motion, gestures, etc. For example, the strain gauge module 202 can be attached to fingernail, toenail, claw, etc., as illustrated and described in greater detail with respect to FIG. 5-7. Alternatively, components of the modular sensor 110 may be fastened to a surface via other means, such as straps, buckles, adhesives, fasteners, magnets, etc.

In exemplary embodiments, the strain gauge module 202 includes one or more strain gauges. The strain gauges may be semiconductor/piezoelectric strain gauges and may be configured in orientations such as quarter-, half-, and full-bridges. In other embodiments, the strain gauges may be foil, photoelectric, thin-film, semiconductor, etc.

In exemplary embodiments, the power cable ribbon 204 may be a communication channel for power and communication between the strain gauge module 202 and the component module 206. In embodiments in which the strain gauge module 202 includes strain gauges, for example, the power cable ribbon 204 may transmit electrical current and resistance measurements measured by the strain gauge module 202 to the component module 206. In embodiments, the power cable ribbon 204 may be detachable from both and/or either the strain gauge module 202 and the component module 206. For example, the detachable connection may be a plug that may be plugged or unplugged in order to detach the component module 206 and the power cable ribbon 204 from the strain gauge module 202 for charging, data transfer, replacement, etc.

In exemplary embodiments, the component module 206 may include a bridge, an amplifier, an analog to digital converter, a microcontroller, a battery, a wireless adapter, memory, Cu traces, accelerometer, gyroscope, antenna, etc. In exemplary embodiments, components of the component module 206 may be spread across the component module 20 in ergonomic and efficient manners. For example, and depicted by FIG. 5-7, the component module 206 may include a microcontroller, memory, Cu traces, accelerometer, gyroscope, antenna, etc., on a top side of a flexible substrate comprising the component module 206 and a flexible thin film battery (single or multiple cells) on a bottom side of the flexible substrate. Depending on application, the component module 206 may be configured in various shapes and sizes in order to contour to a surface or fit within particular constraints. For example, and depicted by FIG. 5-7, the flex circuit may form a ring or bandage shape around a cylindrical object.

The wireless adapter 224 may be configured for connecting to the network 108, and operate in Bluetooth, 2.4 gHz and 5 gHz internet, near-field communication, Z-Wave, Zigbee, etc. The component module 206 is described in greater detail with reference to FIG. 8-10.

Figure 3:
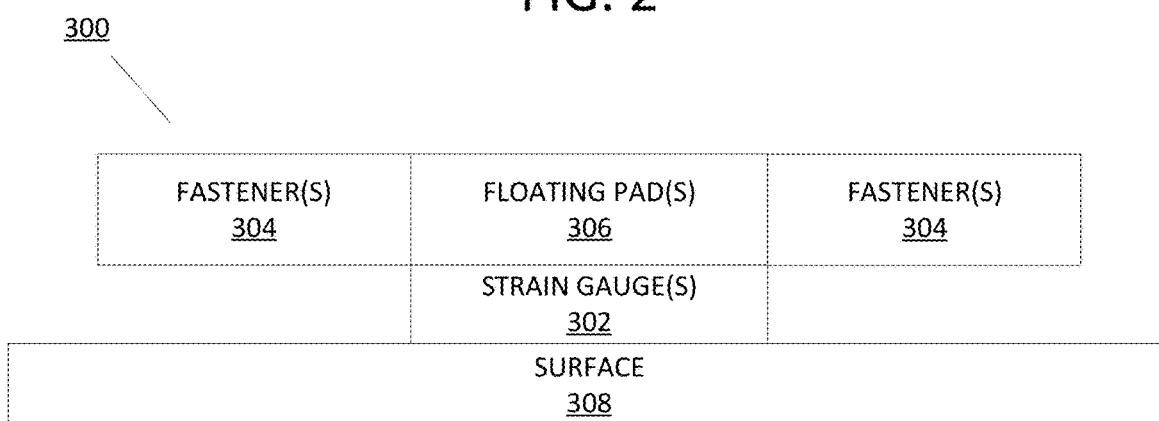
FIG. 3 depicts an exemplary schematic diagram 300 of a strain gauge module 202 of the modular sensor 110, in accordance with the exemplary embodiments.

FIG. 3 depicts an exemplary schematic diagram 300 of a strain gauge module 202 of the modular sensor 110, in accordance with the exemplary embodiments.

In the example embodiment, the strain gauge module 202 includes one or more strain gauges 302, one or more fasteners 304, and one or more floating pads 306. In exemplary embodiments, the one or more strain gauges 302 and the one or more fasteners 304 may make direct contact with a surface 308 for which a strain measurement is desired.

The one or more strain gauges 302 may be semiconductor/piezoelectric strain gauges and may be configured in orientations such as quarter-, half-, and full-bridges. In other embodiments, the one or more strain gauges 302 may be foil, photoelectric, thin-film, etc. While in the exemplary embodiments the strain gauge module 202 is configured for strain gauge type sensors, in other embodiments the strain gauge module 202 may be configured for other type sensors.

The one or more fasteners 304 may be one or more materials capable of securing and maintaining contact between the strain gauge module 202 to the surface 308. Accordingly, the one or more fasteners 304 may adhere to the surface 308 via adhesion, fasteners, straps, belts, buckles, magnets, etc. In general, the one or more fasteners may be any suitable material for fastening the strain gauge module 202, and in general the modular sensor 110, to the surface 308.

The component module 206 may be a module for housing circuitry and processing components of the modular sensor 110. In embodiments, the component module 206 may process signals measured by the strain gauge module 202 and received via the power cable ribbon 204, and may include, for example, a bridge, an amplifier, an analog to digital converter, a microcontroller, a battery, a wireless transmitter, and a battery. The operations of the component module 206 are described in greater detail with respect to FIG. 4-10.

Figure 4:
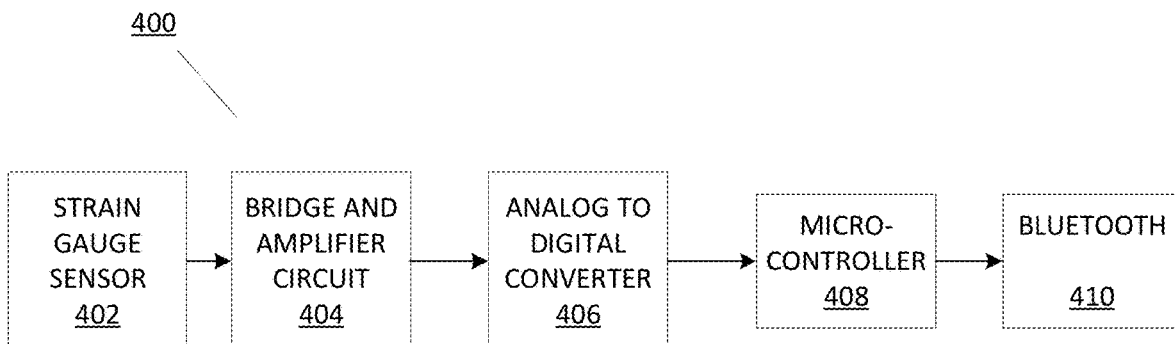
FIG. 4 depicts an exemplary flowchart 400 illustrating the operations of the modular sensor 110 of the modular sensor system 100, in accordance with the exemplary embodiments.

FIG. 4 depicts an exemplary flowchart 400 illustrating the operations of the modular sensor 110 of the modular sensor system 100.

The component module 206 may receive strain gauge sensor data from the strain gauge module 202 via the power cable ribbon 204 at step 402. In the example embodiment, the strain gauge sensor data may be collected by the one or more strain gauges 302 and received as an analog electrical resistance generated during the deformation of the one or more strain gauges 302.

The component module 206 may measure and amplify the received strain gauge sensor data using a bridge and amplifier circuit at step 404. In embodiments, the bridge may be a Wheatstone bridge, a quarter-, half-, full-bridge, etc.

At step 406, the component module 206 may convert the amplified analog signal to a digital signal.

The component module 206 may process the digital data using a microcontroller at step 408. In exemplary embodiments, processing the data involves determining a strain based on the measured, amplified, and converted change in electrical resistance sensed by the one or more strain gauges 302.

At 410, the component module 206 may transmit the processed strain via the network 108, e.g., Bluetooth. The data may be transmitted to, for example, an electronic health record, a patient, a doctor, etc.

Figure 5:
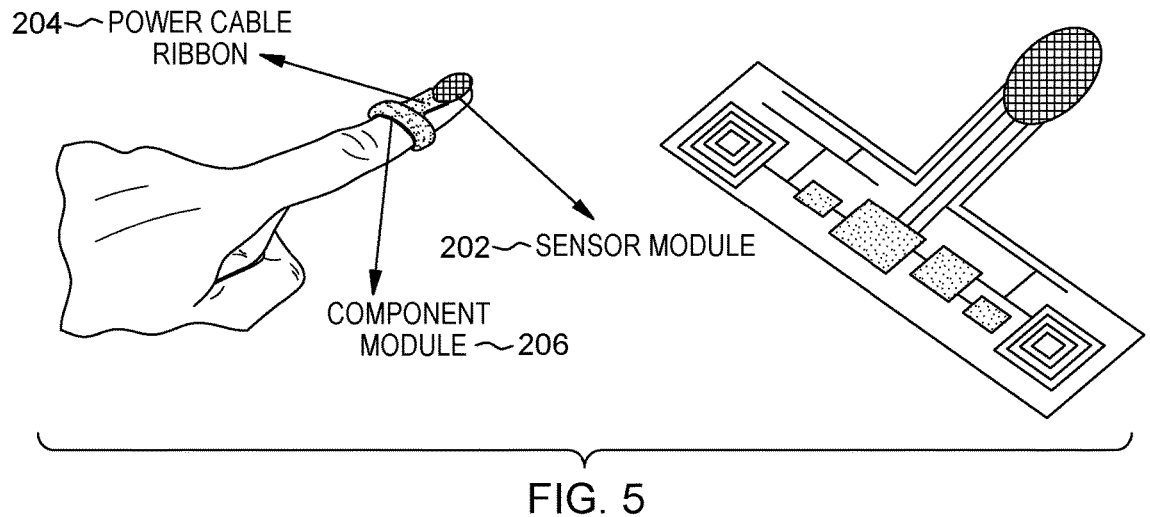
FIG. 5 depicts an exemplary use case of the modular sensor system 100, in accordance with the exemplary embodiments.

FIG. 5 depicts an exemplary use case of the modular sensor system 100, in accordance with the exemplary embodiments. Here, the modular sensor 110 is implemented on a fingernail of a user. As illustrated, the modular sensor 110 comprises the power cable ribbon 202 connecting the component module 206 and the sensor module 202.

Figure 6:
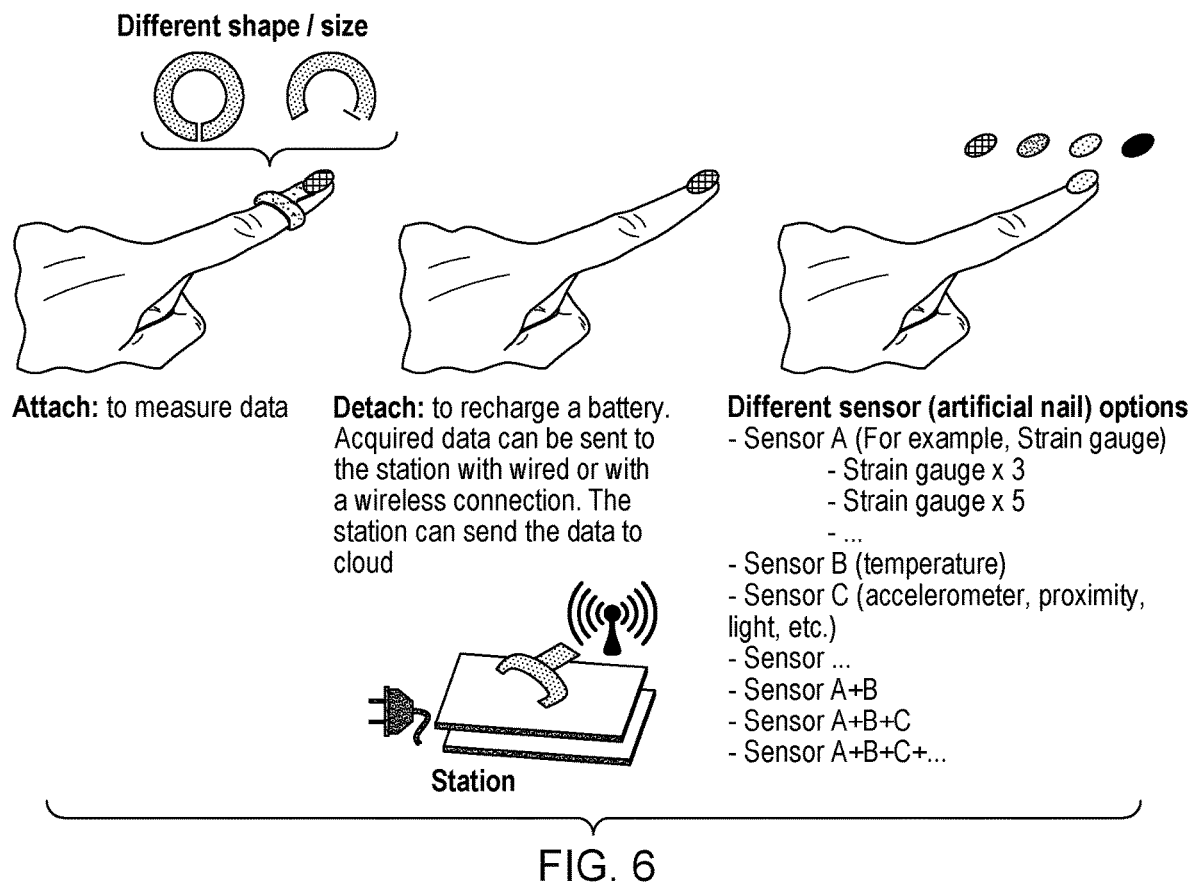
FIG. 6 depicts an exemplary use case of the modular sensor system 100, in accordance with the exemplary embodiments.

FIG. 6 depicts an exemplary use of the modular sensor system 100, in accordance with the exemplary embodiments. As illustrated, the modular sensor 110 may be attached to a surface such as a user fingernail. The power cable ribbon 204 and component module 206 may be removed, leaving only the sensor module 202 on the surface and allowing the component module to be connected to a station for storage, charging, data transfer, etc. Moreover, the sensor module 202 may comprise multiple, differing sensors that may be layered. Also illustrated is the shape of the modular sensor 110, which can be formed around a surface. Here, the component module 206 may be separated from the sensor module 202 and wrapped around a surface in a location that differs from the measuring surface.

FIG. 7 depicts an exemplary use case of the components module 206 of the modular sensor 110, in accordance with the exemplary embodiments. Illustrated here are a top side of the component module 206 on the left comprising a microcontroller, memory, Cu traces, accelerometer, gyroscope, antenna, etc. On the bottom of the component module 206 is a thin film battery. It will be appreciated that in other embodiments, components within the component module 206 may located alternatively.

Figure 8:
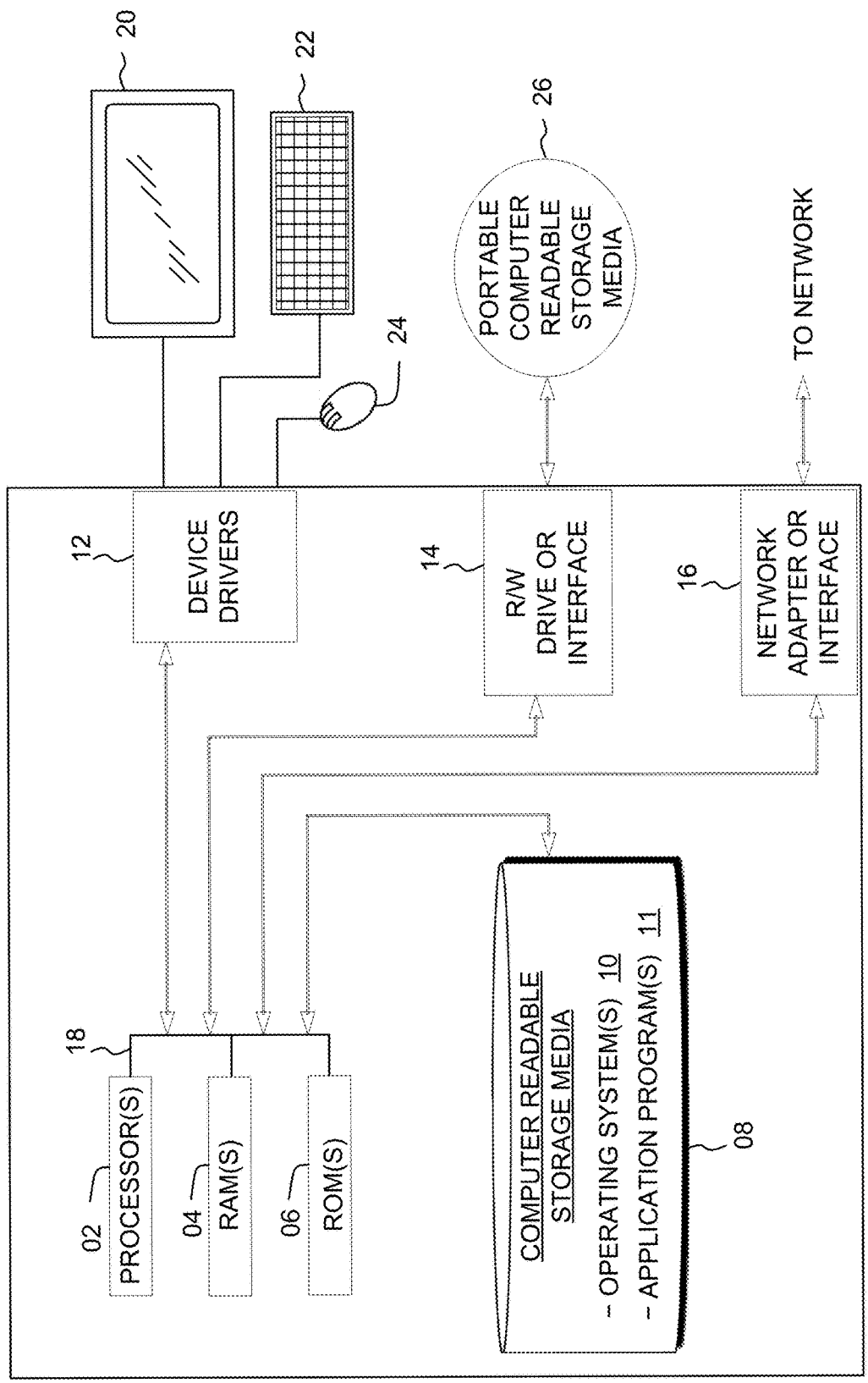
FIG. 8 depicts an exemplary block diagram depicting the hardware components of the modular sensor system 100 of FIG. 1, in accordance with the exemplary embodiments.

FIG. 8 depicts a block diagram of devices within the modular sensor system 100 of FIG. 1, in accordance with the exemplary embodiments. It should be appreciated that FIG. 5 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
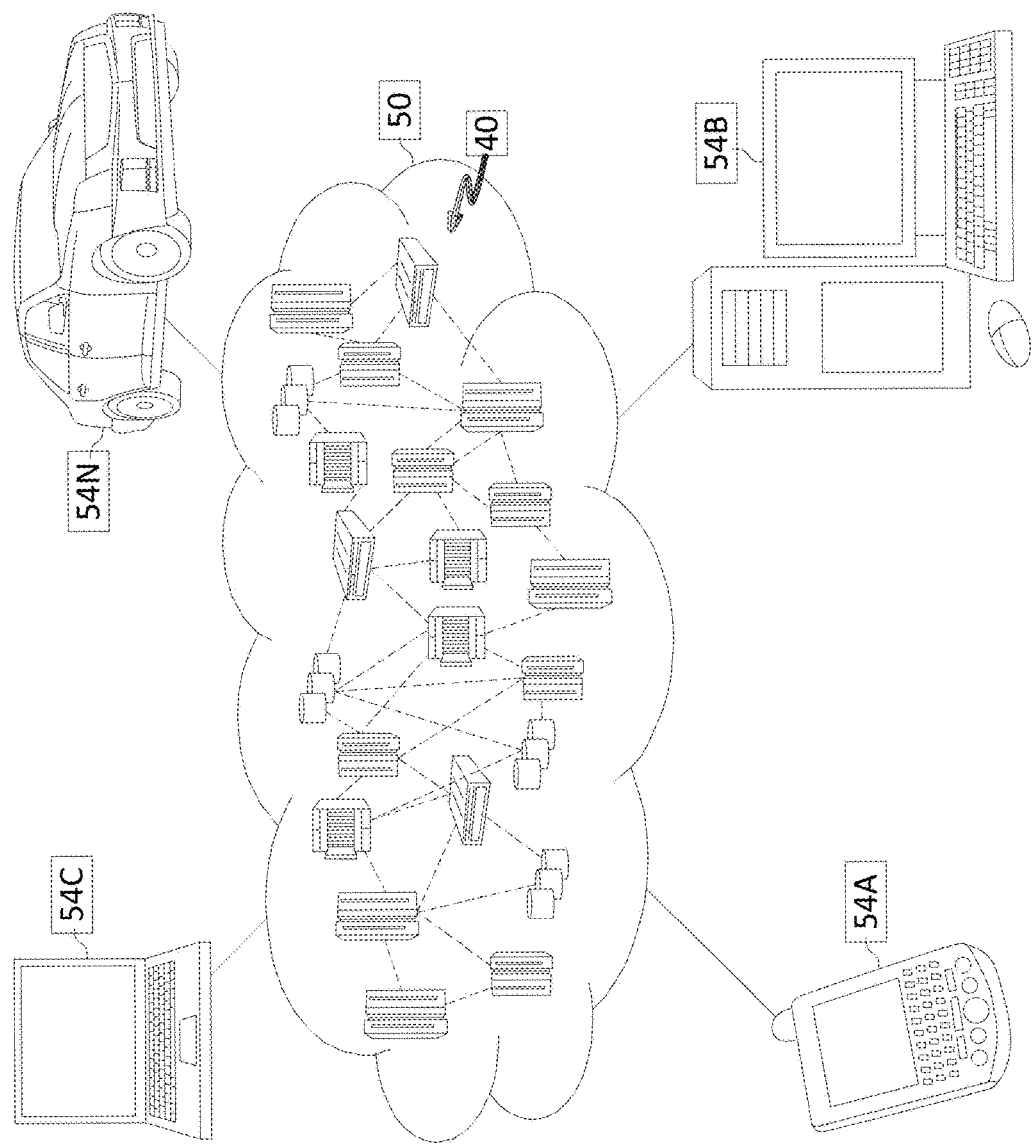
FIG. 9 depicts a cloud computing environment, in accordance with the exemplary embodiments.

Referring now to FIG. 9, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 40 and cloud computing environment 50 can communicate with any type of computerized device over any type of network and/or network addressable connection (e.g., using a web browser).

Figure 10:
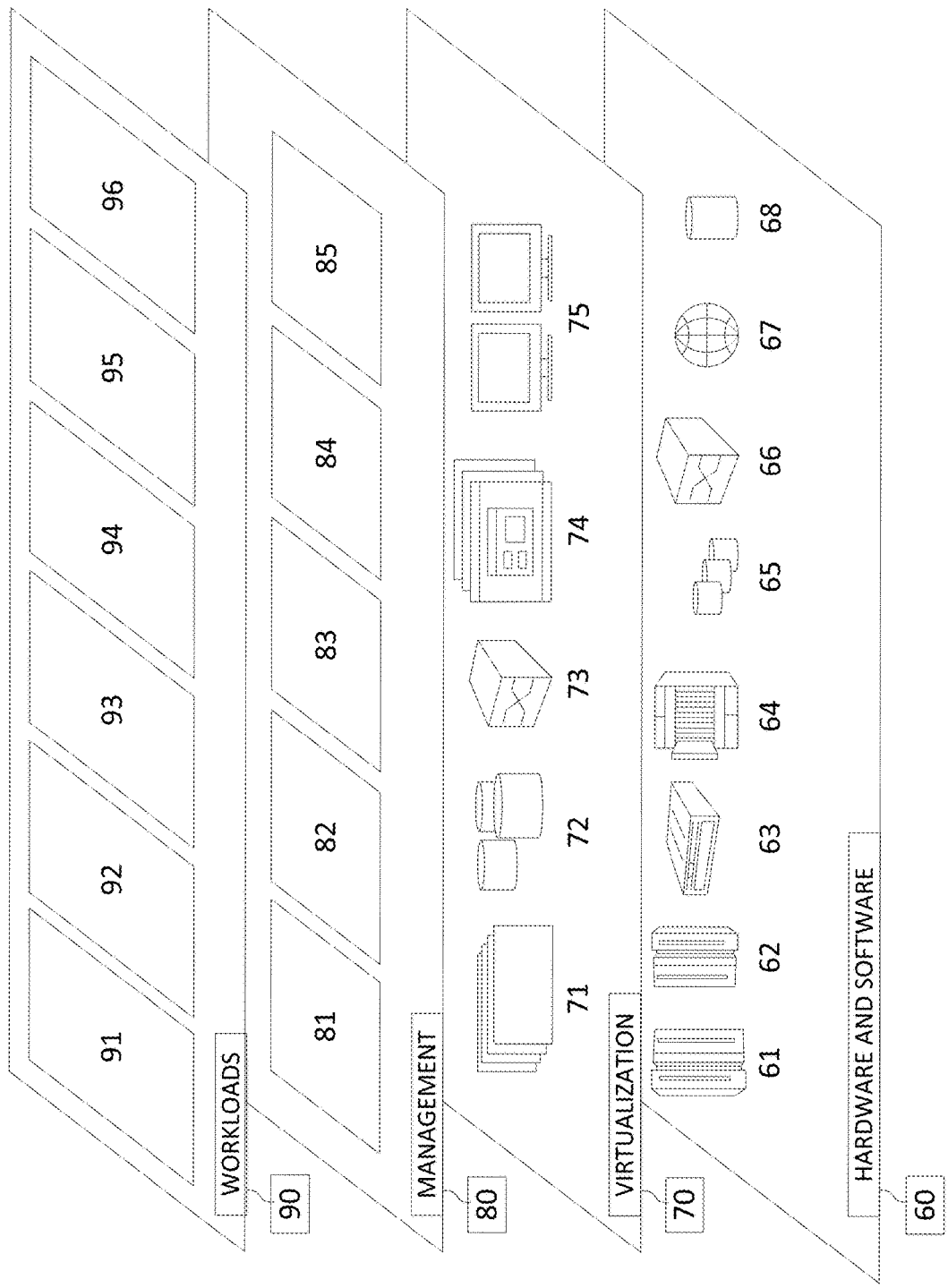
FIG. 10 depicts abstraction model layers, in accordance with the exemplary embodiments.

Referring now to FIG. 10, a set of functional abstraction layers provided by cloud computing environment 50 (FIG. 9) is shown. It should be understood in advance that the components, layers, and functions shown in FIG. 10 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and modular sensor processing 96.

The exemplary embodiments may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A structure of a modular sensing unit, the structure comprising:
 a standalone sensor module for detecting physical properties or biological information, wherein the standalone sensor module includes at least one artificial nail, wherein the artificial nail includes layered sensors including at least one of a temperature sensor, an accelerometer, a gyroscope, an optical sensor, a vibration sensor, a piezoelectric sensor, and a strain gauge;
 a power cable ribbon; and
  a flexible component module, wherein the component module is in communication with and detachable from the artificial nail of the sensor module via the power cable ribbon.

2. The structure of claim 1, wherein the component module comprises a bridge, an amplifier, an analog to digital converter, a microprocessor, and memory.

3. The structure of claim 2, wherein the component module further comprises a battery and a wireless adapter.

4. The structure of claim 1, wherein the sensor module is adhesive and is peelable.

5. The structure of claim 1, wherein the power cable ribbon includes one or more plugs for communication with the sensor module and the component module.

6. The structure of claim 1, further comprising a station unit for receiving at least one of the sensor module, the power cable ribbon, and the component module.

7. The structure of claim 6, wherein the station unit charges the component module.

8. The structure of claim 6, wherein the station unit transfers data from the modular sensing unit to an external source.

9. The structure of claim 1, further comprising:
 a plurality of artificial nails disposed in layers.

10. The structure of claim 9, wherein at least two artificial nails of the plurality of artificial nails are different sensor types from one another.

* * * * *